US00PP33120P2

(12) United States Plant Patent
Van Swieten

(10) Patent No.: US PP33,120 P2
(45) Date of Patent: Jun. 1, 2021

(54) ***PHALAENOPSIS* ORCHID PLANT NAMED 'PHALYPBE'**

(50) Latin Name: ***Phalaenopsis* hybrid**
Varietal Denomination: PHALYPBE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/923,579

(22) Filed: Jul. 8, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variey Database 20210113, retrieved on Jan. 13, 2021, retrieved from the Internet at https://www.upov.int/pluto/en/index.jsp, one page. (Year: 2021).*

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALYPBE', particularly characterized by small, striped, light greenish-yellow flowers with red-purple lips, concave flower shape in lateral view, small bump and ridge on the apical lobe, oblong lateral lobe shape, and is propagated by meristem tissue culture, is disclosed.

3 Drawing Sheets

Genus and species: *Phalaenopsis* hybrid.
Variety denomination: 'PHALYPBE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALYPBE'.

The new *Phalaenopsis* plant is a product of a planned breeding program conducted by the inventor in Bleiswijk, the Netherlands. The objective of this breeding program was to create a new *Phalaenopsis* plant with few branches, small, striped, light greenish-yellow flowers with red-purple lips, suitable for potted plant production.

The new *Phalaenopsis* plant 'PHALYPBE' is a result of cross-pollination made by the inventor in January 2011 in Bleiswijk, the Netherlands, of the proprietary female, or seed parent, *Phalaenopsis* hybrid '21864-012' (unpatented) with the proprietary male, or pollen parent, *Phalaenopsis* hybrid '01-3358' (unpatented).

The new *Phalaenopsis* was selected by the inventor as a single plant within the progeny of the stated cross-pollination in a controlled greenhouse in Bleiswijk, the Netherlands, in April 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2072), by Applicant who obtained the subject matter disclosed directly from the inventor. 'PHALYPBE' has not been made publicly available or sold anywhere in the world prior to the effective filing date of this application with the exception of sales or disclosures made one year or less before the effective filing date of this claimed invention by Applicant who obtained 'PHALYPBE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALYPBE' as a new and distinct variety of *Phalaenopsis* plant:

1) Small, striped, light greenish-yellow flowers with red-purple lips;
2) Flower shape in lateral view is concave;
3) Flower has a small bump and ridge on the apical lobe; and
4) Lateral lobe shape is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in May 2020. Colors in the photographs may differ from the color values cited in the detailed botanical description, which accurately describe the actual colors of the new variety.

DESCRIPTION OF THE NEW VARIETY

Figure 1:
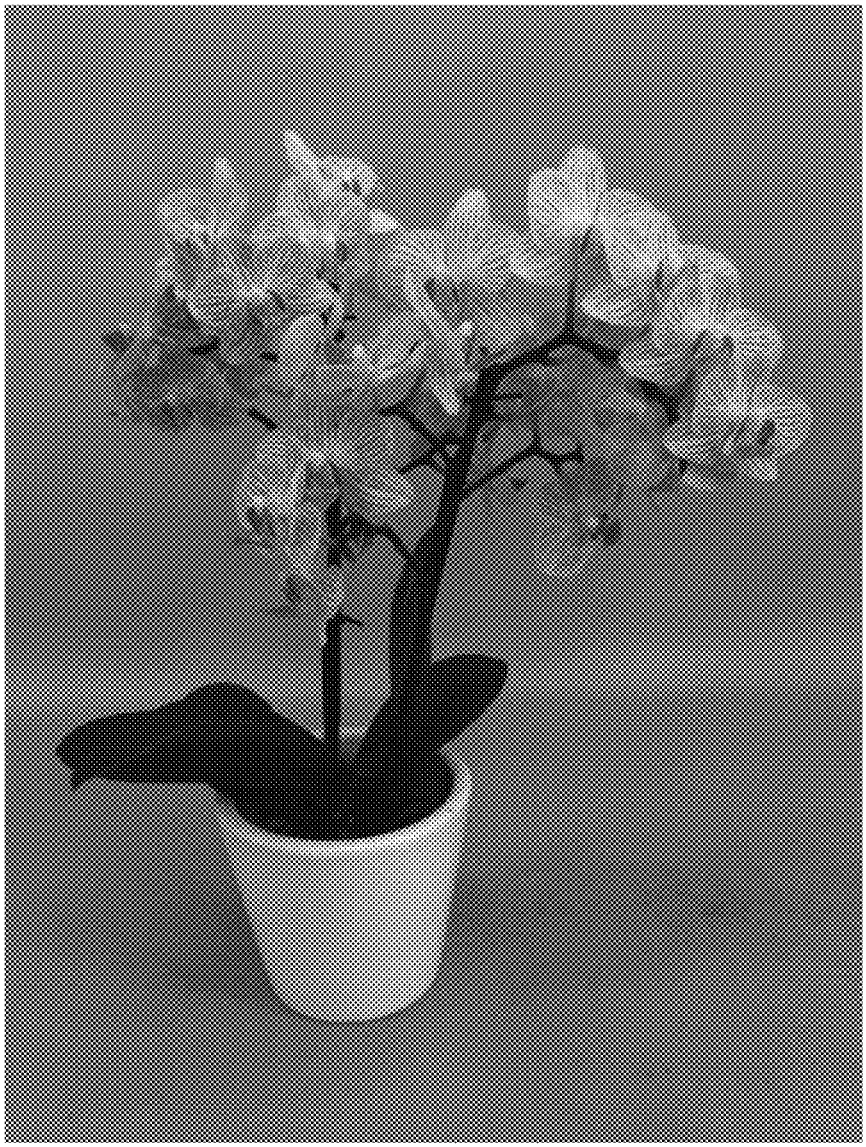
FIG. 1 shows the overall plant habit, including blooms and foliage of 'PHALYPBE'.
Figure 2:
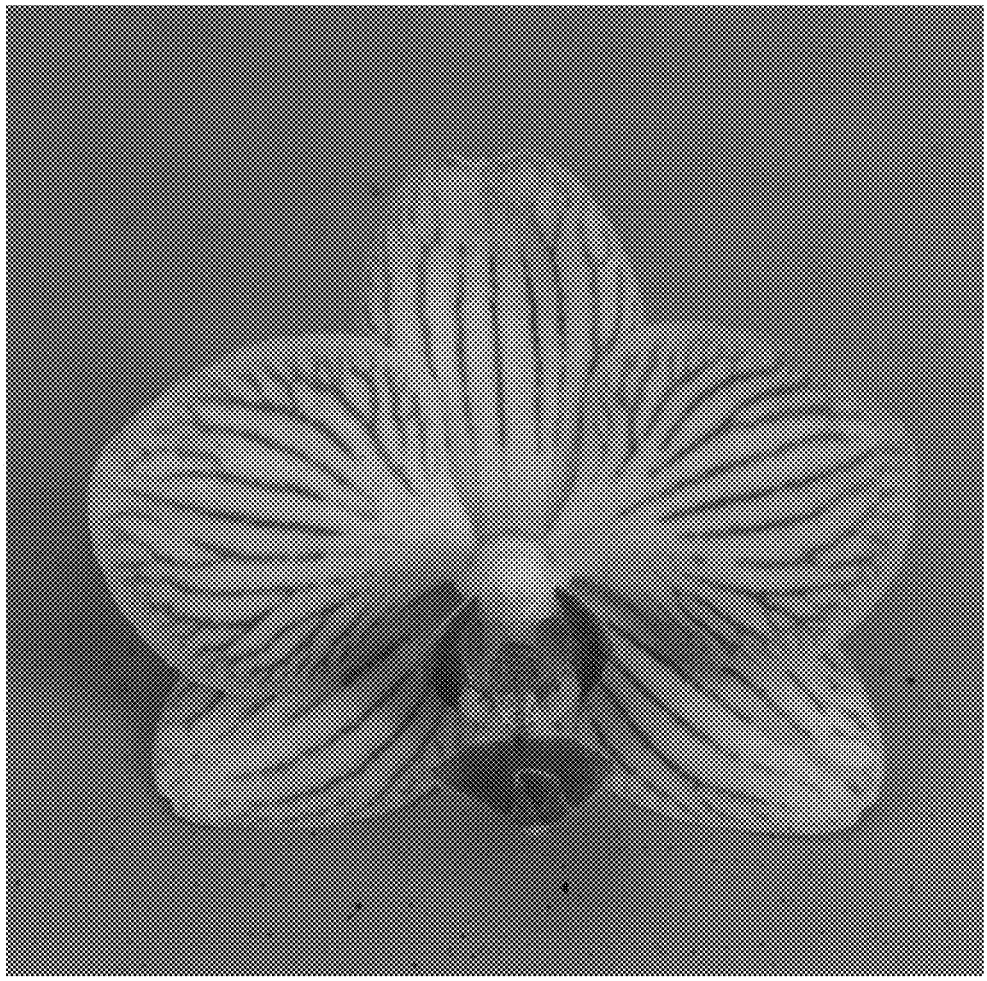
FIG. 2 shows a close-up of a flower of 'PHALYPBE'.
Figure 3:
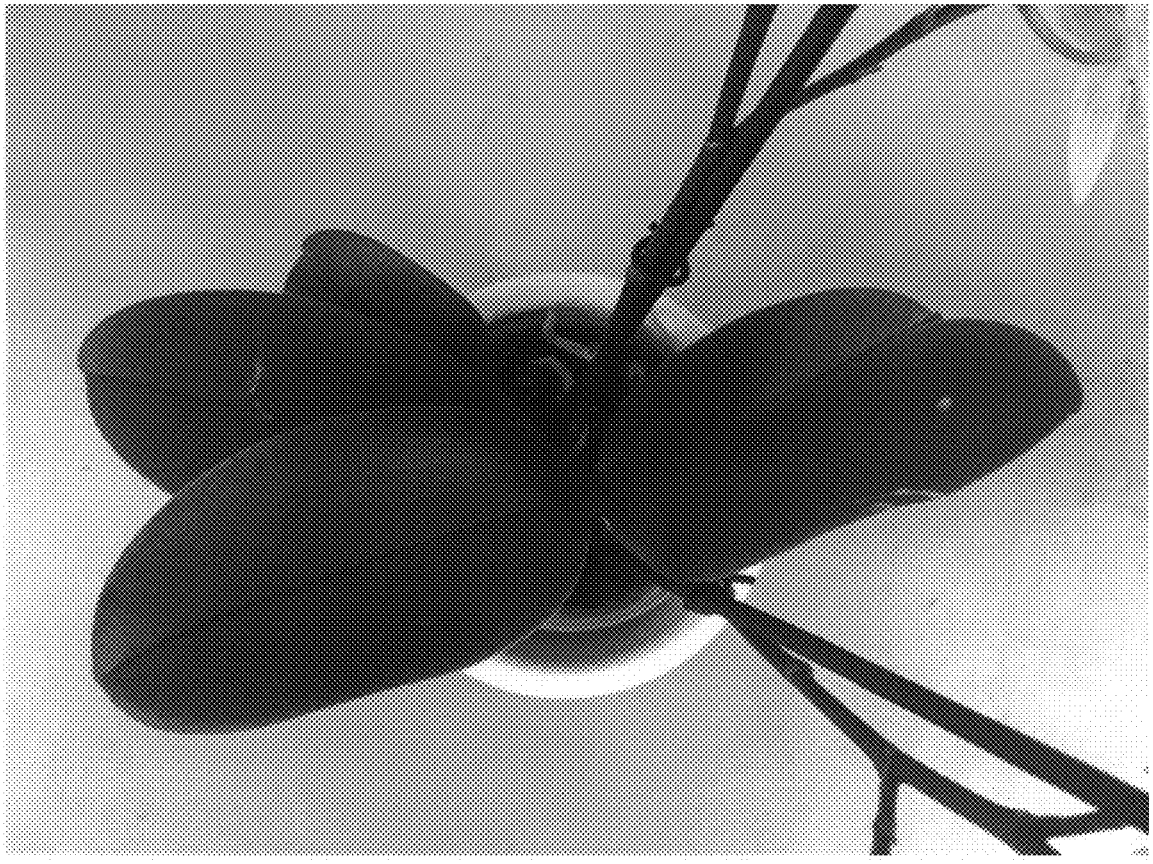
FIG. 3 shows an overhead view of the leaves of 'PHALYPBE'.

The following detailed description sets forth the distinctive characteristics of 'PHALYPBE'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2020 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALYPBE'.

Parentage:

*Female parent*.—*Phalaenopsis* cultivar '21864-012' (unpatented).

*Male parent*.—*Phalaenopsis* cultivar '01-3358' (unpatented).

Propagation:

*Type*.—Meristem tissue culture.

Roots:

*Root description*.—Greyed-green (something between RHS 190B and 190C) colored roots with branching lateral roots having yellow-green (RHS 144C) colored root tips.

Plant:

*Commercial crop time to flowering*.—Following asexual propagation (in vitro), the rooted cuttings grow for 18-20 weeks. After transplantation into 9-cm pots, the plants are finished after 40 to 42 weeks.

*Growth habit of the peduncle*.—Upright to slightly pendent with panicle inflorescence.

*Height (from soil level to top of inflorescence)*.—Approximately 27.0 cm to 32.0 cm.

*Width (measured from leaf tips)*.—About 21.0 cm to 24.0 cm.

*Vigor*.—Strong.

Leaves:

*Mature leaves*.—Quantity per plant: 7 to 9 leaves are produced before flowering. Length (fully expanded): 12.0 cm to 14.0 cm. Width: 5.5 cm to 6.5 cm. Position of the broadest part of the leaf: At the middle. Shape: Oblong. Base shape: Moderately elongated. Apex: Obtuse unequal. Leaf blade angle with the petiole (measured from the horizontal position): Between 5 degrees and 15 degrees. Leaf margin: Entire. Color: Upper surface: RHS 146A. Lower surface: RHS 146B with a touch of RHS 187A toward the margin. Texture (both upper and lower surfaces): Smooth. Thickness: 2.0 mm to 2.2 mm. Variegation: Absent. Venation: Pattern: Parallel. Color of the midvein: Upper surface: RHS 146A. Lower surface: Diluting RHS 187A.

Peduncle:

*Quantity per plant*.—1 to 3.

*Number of flowers per peduncle*.—18 to 23.

*Length*.—27.0 cm to 32.0 cm.

*Diameter*.—3.6 mm to 4.0 mm.

*Strength*.—Strong.

*Aspect*.—Upright to slightly pendent.

*Texture*.—Smooth.

*Color*.—Mix of brown (RHS 200B) and yellow-green (RHS 146C).

*Internode length*.—1.5 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 160.0 mm to 200.0 mm.

*Flowering time*.—First flowers can be expected 10 to 11 months after planting in a 9-cm pot.

*Flower*.—Height: 40.0 mm to 45.0 mm. Diameter: 47.0 mm to 52.0 mm. Depth of lip: 15.0 mm to 17.0 mm.

*Flower longevity*.—On the plant: 11 to 13 weeks.

*Flower shape*.—Concave.

*Fragrance*.—Absent.

*Flower bud*.—Average size: Medium. Length: 16.0 mm to 18.0 mm. Width: 13.0 mm to 15.0 mm. Shape: Egg shaped. Color: Yellowish-green (RHS N144A).

*Petals*.—Arrangement: Open/free. Shape: Semi-circular. Apex: Rounded asymmetric. Margin: Entire. Length (from base to tip): 22.0 mm to 24.0 mm. Width: 24.0 mm to 26.0 mm. Position of the broadest part of the petal: Toward the base. Color (when fully opened): Upper surface: Basic color: Light greenish-yellow (RHS 4B). Over color: Red stripes (RHS 184A). Lower surface: Basic color: Light greenish-yellow (RHS 4C). Over color: Light yellow-green (RHS 4D) at the base; diluting stripes (RHS 184D). Number of spots and stripes on the petals (upper surface): Many stripes. Color of spots and stripes on the petals (upper surface): RHS 184A. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 25.0 mm to 27.0 mm. Width: 27.0 mm to 29.0 mm. Position of the broadest part of the dorsal sepals: At the middle. Color (when fully opened): Upper surface: Basic color: Greenish-yellow (something in between RHS 4A and 4B). Over color: Light yellow-green (RHS 145C) at the base. Lower surface: Basic color: Light greenish-yellow (something in between RHS 4B and 4C). Over color: Yellow-green (RHS 154C). Number of spots and stripes on the dorsal sepals (upper surface): Medium to many stripes. Color of spots and stripes on the dorsal sepals (upper surface): RHS 184A. Density of netting of the dorsal sepals (upper surface): None. Color of the netting: Not applicable.

*Lateral sepals*.—Shape: Ovate. Apex: Emarginated symmetric. Margin: Entire. Length (from base to tip): 25.0 mm to 27.0 mm. Width: 19.0 mm to 21.0 mm. Position of the broadest part of the lateral sepals: Toward the base. Color (when fully opened): Upper surface: Basic color: Light greenish-yellow (something in between RHS 4B and 4C). Over color: Hint of light yellow-green (something in between RHS 145B and 145C) at the base. Lower surface: Basic color: Light greenish-yellow (RHS 4B). Over color: Yellow-green (RHS 154C). Number of spots and stripes on the lateral sepals (upper surface): Medium to many stripes. Color of spots and stripes on the lateral sepals (upper surface): RHS 184A. Density of netting of the lateral sepals (upper surface): None. Color of the netting (upper surface): Not applicable.

*Labellum* (*lip*).—Whiskers: Present. Length of whiskers: 4.0 mm to 5.0 mm. Color of whiskers: Purplish-pink (RHS N78C) at the base and white (RHS NN155C) toward the tip. Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Entire. Length: 12.0 mm to 14.0 mm. Width: 4.0 mm to 5.0 mm. Color: Upper surface: Hint of yellow (RHS 14B and 10C) at the base; white (RHS NN155C) toward margin on one side and reddish-purple (something in between RHS N78A and N78B) toward the margin on the other side Lower surface: Hint of light yellow (RHS 10C) at the base; white (RHS NN155A) toward margin on one side; red (RHS 59A) and reddish-purple (RHS N78A) toward the other side. Number of spots and stripes on the lateral lobe: Medium stripes at the base. Color of spots and stripes on the lateral lobe: Red (RHS 183C). Density of netting of the lateral lobe: None. Color of the netting: None.

*Apical lobe*.—Shape: Rhombic. Margin: Entire. Length: 15.0 mm to 17.0 mm. Width: 16.0 mm to 18.0 mm. Bump and ridge: Present (small). Color: Upper surface: Yellow (RHS 14A) at the base; red (RHS 184A) and reddish-purple (RHS N78A to N78B) toward whiskers. Lower surface: Yellow (RHS 14B) toward the wings on both sides; white (RHS NN155C) at the middle and purplish-pink (RHS N78C) at margins toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Very small. Height: 0.3 cm to 0.4 cm. Length: 0.2 cm to 0.3 cm. Width: 0.3 cm to 0.4 cm. Color: Yellow (RHS 14A); dotted (RHS 176A).

Reproductive organs:

*Column*.—Length: 8.0 mm to 9.0 mm. Diameter: 3.8 mm to 4.2 mm. Color: Very light purple (RHS 76B) at the base and white tip (RHS NN155C).

*Pollinia*.—Quantity: 2. Diameter: 0.5 mm to 0.7 mm. Color: Orange-yellow (RHS 17A).

*Ovary*.—Length: 8.0 mm to 10.0 mm. Diameter: 1.8 mm to 2.0 mm.

*Pedicel*.—Length: 30.0 mm to 32.0 mm. Diameter: 2.1 mm to 2.3 mm. Texture: Smooth. Color: Yellow-green (RHS 144B) at the base; light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALYPBE' differs from female parent plant '21864-012' (unpatented) in that 'PHALYPBE' has flowers with a main color of light greenish-yellow and rhombic apical lobes, whereas '21864-012' has flowers with a main color of greenish-yellow and narrowly rhombic apical lobes.

'PHALYPBE' differs from male parent plant '01-3358' (unpatented) in that 'PHALYPBE' has flowers with a main color of light greenish-yellow, oblong lateral lobes, and rhombic apical lobes, whereas '01-3358' has flowers with a main color of purplish-pink, weakly spatulate lateral lobes, and triangular to ovate apical lobes.

'PHALYPBE' is most similar to the commercial *Phalaenopsis* plants named 'PHALFOMZYN' (U.S. Plant Pat. No. 31,947) and 'PHALGALYI' (U.S. Plant Pat. No. 31,051). 'PHALYPBE' differs from the commercial variety 'PHALFOMZYN' in that 'PHALYPBE' has a striped flower pattern, rhombic apical lobes, and whiskers that are purplish-pink at the base and white toward the tip, whereas 'PHALFOMZYN' has a dotted flower pattern, elliptic to circular apical lobes, and white whiskers.

'PHALYPBE' differs from the commercial variety 'PHALGALYI' in that 'PHALYPBE' has rhombic apical lobes and whiskers that are purplish-pink at the base and white toward the tip, whereas 'PHALGALYI' has ovate apical lobes and greenish-yellow whiskers. Additionally, 'PHALYPBE' has smaller flowers than 'PHALGALYI'.

I claim:

1. A new and distinct variety of *Phalaenopsis* plant named 'PHALYPBE', substantially as described and illustrated herein.

* * * * *